(12) United States Patent  
Machado (10) Patent No.: US 9,211,408 B2  
(45) Date of Patent: Dec. 15, 2015

(54) SYSTEM AND METHOD FOR NEUROMODULATION USING COMPOSITE PATTERNS OF STIMULATION OR WAVEFORMS

(71) Applicant: THE CLEVELAND CLINIC FOUNDATION, Cleveland, OH (US)

(72) Inventor: Andre Machado, Beachwood, OH (US)

(73) Assignee: The Cleveland Clinic Foundation, Cleveland, OH (US)

(\*) Notice: Subject to any disclaimer, the term of this patent is extended or adjusted under 35 U.S.C. 154(b) by 157 days.

(21) Appl. No.: 13/776,875

(22) Filed: Feb. 26, 2013

(65) Prior Publication Data
US 2013/0338726 A1 Dec. 19, 2013

Related U.S. Application Data

(63) Continuation-in-part of application No. 13/365,549, filed on Feb. 3, 2012, which is a continuation of application No. 11/943,344, filed on Nov. 20, 2007, now Pat. No. 8,112,154, which is a (Continued)

(51) Int. Cl.
*A61N 1/36* (2006.01)
*A61N 1/05* (2006.01)
(Continued)

(52) U.S. Cl.
CPC ........ *A61N 1/36025* (2013.01); *A61N 1/36017* (2013.01); *A61N 1/36067* (2013.01);
(Continued)

(58) Field of Classification Search
CPC .............. A61N 1/0529; A61N 1/0534; A61N 1/36017; A61N 1/36025; A61N 1/36103; A61N 1/36189; A61B 5/04001; A61B 5/1118

USPC ........................................... 607/5, 45–46, 57
See application file for complete search history.

(56) References Cited

U.S. PATENT DOCUMENTS 4,151,470 A 4/1979 Sato
4,156,259 A 5/1979 Sato
(Continued)

FOREIGN PATENT DOCUMENTS

| EP | 1559369 A1 | 3/2005 |
| WO | WO 97/39797 | 10/1997 |
| WO | WO 2006/113305 A2 | 10/2006 |

OTHER PUBLICATIONS

International PCT Search Report and Written Opinion, mailed May 7, 2013, pp. 1-11.
Caffrey, Deep Brain Stim . . . and a Structured Review, Pain Med., vol. 2, No. 3, 2001, pp. 183-190.
Mirone, et al, Peripheral Median Nerve . . . Carpal Tunnel Surgery, Jnl of Clin Neurosci., 16 (2009) pp. 825-827.
Calenbergh, at al., Long Term Olin, Outcome . . . Neuropathic Pain., Sur. Neurology 72 (2009) pp. 330-335.

(Continued)

*Primary Examiner* — Amanda Patton
(74) *Attorney, Agent, or Firm* — Tarolli, Sundheim, Covell & Tummino LLP (57) ABSTRACT

A neurostimulation system can include a memory, a playback system, a stimulation electrode, and a controller. The memory can store data for first and second input waveforms. The playback system can provides first and second output waveforms, based on the first and second input waveforms in the memory, respectively, to form composite patterns of stimulation or waveforms. The first output waveform can be different than the second output waveform. The second output waveform can be periodically superimposed on the first output waveform. The controller can be in communication with the stimulation electrode. The controller can be configured to control application of the composite pattern of stimulation or waveform to a target site in a body of a subject suffering from a medical condition.

24 Claims, 8 Drawing Sheets

Related U.S. Application Data continuation-in-part of application No. 11/522,029, filed on Sep. 15, 2006, now Pat. No. 7,715,912, which is a continuation-in-part of application No. 11/404,006, filed on Apr. 13, 2006, now Pat. No. 8,082,033.

(60) Provisional application No. 60/671,011, filed on Apr. 13, 2005, provisional application No. 61/604,730, filed on Feb. 29, 2012.

(51) Int. Cl.
A61B 5/04 (2006.01)
A61B 5/11 (2006.01)

(52) U.S. Cl.
CPC ......... *A61N1/36189* (2013.01); *A61B 5/04001* (2013.01); *A61B 5/1118* (2013.01); *A61N 1/0529* (2013.01); *A61N 1/0534* (2013.01); *A61N 1/36103* (2013.01)

(56) References Cited

U.S. PATENT DOCUMENTS

| | | | |
|---|---|---|---|
| 4,180,821 A | 12/1979 | Prewitt, Jr. et al. | |
| 4,424,812 A | 1/1984 | Lesnick | |
| 4,543,955 A | 10/1985 | Schroeppel | |
| 4,598,713 A | 7/1986 | Hansjurgens et al. | |
| 4,651,740 A | 3/1987 | Schroeppel | |
| 4,699,143 A | 10/1987 | Dufresne et al. | |
| 4,841,973 A | 6/1989 | Stecker | |
| 5,222,494 A | 6/1993 | Baker, Jr. | |
| 5,304,206 A | 4/1994 | Baker, Jr. et al. | |
| 5,354,320 A | 10/1994 | Schaldach et al. | |
| 5,433,736 A | 7/1995 | Nilsson | |
| 5,503,158 A | 4/1996 | Coppock et al. | |
| 5,593,427 A | 1/1997 | Gliner et al. | |
| 5,601,612 A | 2/1997 | Gliner et al. | |
| 5,607,454 A | 3/1997 | Cameron et al. | |
| 5,607,460 A | 3/1997 | Kroll et al. | |
| 5,620,470 A | 4/1997 | Gliner et al. | |
| 5,749,904 A | 5/1998 | Gliner et al. | |
| 5,749,905 A | 5/1998 | Gliner et al. | |
| 5,851,223 A | 12/1998 | Liss et al. | |
| 5,891,178 A | 4/1999 | Munn et al. | |
| 5,978,713 A | 11/1999 | Prutchi et al. | |
| 6,016,449 A | 1/2000 | Fischell et al. | |
| 6,029,090 A | 2/2000 | Herbst | |
| 6,044,301 A | 3/2000 | Hartlaub et al. | |
| 6,061,593 A | 5/2000 | Fischell et al. | |
| 6,128,538 A | 10/2000 | Fischell et al. | |
| 6,198,971 B1 | 3/2001 | Leyseiffer | |
| 6,208,896 B1 | 3/2001 | Mulhauser | |
| 6,249,703 B1 | 6/2001 | Stanton | |
| 6,253,109 B1 | 6/2001 | Gielen | |
| 6,263,246 B1 | 7/2001 | Goedeke | |
| 6,289,247 B1 | 9/2001 | Faltys | |
| 6,308,099 B1 | 10/2001 | Fox | |
| 6,354,299 B1 | 3/2002 | Fischell et al. | |
| 6,393,325 B1 | 5/2002 | Mann et al. | |
| 6,418,346 B1 | 7/2002 | Nelson et al. | |
| 6,442,432 B2 | 8/2002 | Lee | |
| 6,507,759 B1 | 1/2003 | Prutchi et al. | |
| 6,516,227 B1 | 2/2003 | Meadows et al. | |
| 6,539,263 B1 | 3/2003 | Schiff et al. | |
| 6,560,490 B2 | 5/2003 | Grill et al. | |
| 6,579,280 B1 | 6/2003 | Kovach et al. | |
| 6,587,724 B2 | 7/2003 | Mann | |
| 6,609,031 B1 | 8/2003 | Law et al. | |
| 6,622,045 B2 | 9/2003 | Snell et al. | |
| 6,622,050 B2 | 9/2003 | Thompson | |
| 6,628,989 B1 | 9/2003 | Penner et al. | |
| 6,631,297 B1 | 10/2003 | Mo | |
| 6,654,642 B2 | 11/2003 | North et al. | |
| 6,657,106 B2 | 12/2003 | Smith et al. | |
| 6,662,049 B1 | 12/2003 | Miller | |
| 6,662,053 B2 | 12/2003 | Borkan | |
| 6,681,136 B2 | 1/2004 | Schuler et al. | |
| 6,684,106 B2 | 1/2004 | Herbst | |
| 6,690,974 B2 | 2/2004 | Archer et al. | |
| 6,692,315 B1 | 2/2004 | Soumillon et al. | |
| 6,714,812 B1 | 3/2004 | Karjalainen | |
| 6,731,986 B2 | 5/2004 | Mann | |
| 6,748,276 B1 | 6/2004 | Daignault, Jr. et al. | |
| 6,775,573 B2 | 8/2004 | Schuler et al. | |
| 6,778,858 B1 | 8/2004 | Peeters | |
| 6,804,558 B2 | 10/2004 | Haller et al. | |
| 6,850,802 B2 | 2/2005 | Holsheimer | |
| 6,934,580 B1* | 8/2005 | Osorio et al. | 600/545 |
| 6,937,891 B2 | 8/2005 | Leinders et al. | |
| 6,937,903 B2 | 8/2005 | Schuler et al. | |
| 6,944,501 B1 | 9/2005 | Pless | |
| 6,950,706 B2 | 9/2005 | Rodriguez et al. | |
| 6,957,106 B2 | 10/2005 | Schuler et al. | |
| 7,006,859 B1 | 2/2006 | Osorio et al. | |
| 7,008,413 B2 | 3/2006 | Kovach et al. | |
| 7,058,446 B2 | 6/2006 | Schuler et al. | |
| 7,082,333 B1 | 7/2006 | Bauhahn et al. | |
| 7,092,760 B2 | 8/2006 | Foster et al. | |
| 7,110,820 B2 | 9/2006 | Tcheng et al. | |
| 7,127,297 B2 | 10/2006 | Law et al. | |
| 7,142,923 B2 | 11/2006 | North et al. | |
| 7,191,010 B2 | 3/2007 | Ohta et al. | |
| 7,191,014 B2 | 3/2007 | Kobayashi et al. | |
| 7,209,788 B2 | 4/2007 | Nicolelis | |
| 7,216,000 B2 | 5/2007 | Sieracki et al. | |
| 7,228,179 B2 | 6/2007 | Campen et al. | |
| 7,239,916 B2 | 7/2007 | Thompson et al. | |
| 7,254,445 B2 | 8/2007 | Law et al. | |
| 7,266,412 B2 | 9/2007 | Stypulkowski | |
| 7,308,302 B1* | 12/2007 | Schuler et al. | 607/2 |
| 7,483,748 B2 | 1/2009 | Torgerson | |
| 7,715,912 B2 | 5/2010 | Rezai et al. | |
| 8,112,154 B2 | 2/2012 | Rezai et al. | |
| 2003/0060860 A1 | 3/2003 | Foster et al. | |
| 2003/0093129 A1 | 5/2003 | Nicolelis et al. | |
| 2003/0149457 A1 | 8/2003 | Tcheng et al. | |
| 2003/0204221 A1 | 10/2003 | Rodriguez et al. | |
| 2003/0204224 A1 | 10/2003 | Torgerson et al. | |
| 2003/0204226 A1 | 10/2003 | Acosta et al. | |
| 2003/0208244 A1 | 11/2003 | Stein et al. | |
| 2003/0212439 A1 | 11/2003 | Schuler et al. | |
| 2004/0049241 A1 | 3/2004 | Campos | |
| 2004/0098067 A1 | 5/2004 | Ohta et al. | |
| 2005/0021090 A1 | 1/2005 | Schuler et al. | |
| 2005/0228461 A1 | 10/2005 | Osorio et al. | |
| 2005/0251061 A1 | 11/2005 | Schuler et al. | |
| 2005/0261061 A1 | 11/2005 | Nguyen et al. | |
| 2005/0261601 A1 | 11/2005 | Schuler et al. | |
| 2005/0261747 A1 | 11/2005 | Schuler et al. | |
| 2005/0288732 A1 | 12/2005 | Schuler et al. | |
| 2006/0155340 A1 | 7/2006 | Schuler et al. | |
| 2006/0206169 A1 | 9/2006 | Schuler | |
| 2006/0239482 A1 | 10/2006 | Hatoum | |
| 2006/4224189 | 10/2006 | Schuler at al. | |
| 2007/0078498 A1 | 4/2007 | Rezai et al. | |
| 2007/0100377 A1 | 5/2007 | Armstrong et al. | |
| 2007/0142874 A1 | 6/2007 | John | |
| 2007/0191887 A1 | 8/2007 | Schuler et al. | |
| 2007/0203532 A1 | 8/2007 | Tass et al. | |
| 2008/0208284 A1 | 8/2008 | Rezai et al. | |
| 2012/0059438 A1 | 3/2012 | De Ridder | |
| 2012/0136410 A1 | 5/2012 | Rezai et al. | |

OTHER PUBLICATIONS

PCT International Search Report and the Written Opinion of the Int'l Searching Authority for PCT/US2008/084212, pp. 1-12.

International Search Report and Written Opinion for PCT/US2014/018204, mailed Jun. 11, 2014, pp. 1-13.

* cited by examiner

SYSTEM AND METHOD FOR NEUROMODULATION USING COMPOSITE PATTERNS OF STIMULATION OR WAVEFORMS

RELATED APPLICATIONS

This application is a continuation-in-part (CIP) of U.S. patent application Ser. No. 13/365,549, filed Feb. 3, 2012, which is a continuation of U.S. patent application Ser. No. 11/943,344, filed Nov. 20, 2007 (now U.S. Pat. No. 8,112,154), which is a CIP of U.S. patent application Ser. No. 11/522,029, filed Sep. 15, 2006 (now U.S. Pat. No. 7,715,912), which is a CIP of U.S. patent application Ser. No. 11/404,006, filed Apr. 13, 2006 (now U.S. Pat. No. 8,082,033), which claims the benefit of U.S. Provisional Patent Application Ser. No. 60/671,011, filed Apr. 13, 2005. This application also claims the benefit of U.S. Provisional Patent Application Ser. No. 61/604,730, filed Feb. 29, 2012. The entirety of each of the aforementioned applications is hereby incorporated by reference for all purposes.

TECHNICAL FIELD

The present disclosure relates generally to neuromodulation using electrical stimulation, and more particularly to neuromodulation using composite patterns of stimulation or waveforms to treat medical conditions.

BACKGROUND

Debilitating movement disorders have been treated by non-reversible surgical ablation of affected brain circuits by thalamotomy or pallidotomy, for example. Deep brain stimulation (DBS) therapy is an attractive alternative to such permanent surgeries, providing the distinct advantages of reversibility and adjustability of treatment over time. DBS is a treatment method that aims to change the rates and patterns of activity of brain cells by implanting a brain stimulator (i.e., an electrode, also known as a lead) into a target region in the brain known to be associated with movement, such as the thalamus, subthalamic nucleus (STN), globus pallidus, internal capsule, and nucleus accumbens.

Electrical stimulation by DBS of a particular target region of the brain, in some cases bilaterally (i.e., using an electrode on each side of the brain to stimulate paired target regions located on each side of the brain), has been successfully used to treat symptoms of several movement disorders. For example, it has been reported in several studies that targeting of the STN is effective to alleviate symptoms of Parkinson's disease. To date, all DBS applied to humans in FDA-approved clinical trials are conducted with regular isochronous stimulation; that is, the pulses of electrical stimulation are evenly distributed in time. Parkinson's disease and essential tremor, for example, are typically treated with high frequency isochronous stimulation at 130 Hz or greater.

SUMMARY

One aspect of the present disclosure can include a neurostimulation system.

The neurostimulation system can comprise a memory, a playback system, a stimulation electrode, and a controller. The memory can store data for first and second input waveforms. The playback system can provides first and second output waveforms, based on the first and second input waveforms in the memory, respectively, to form composite patterns of stimulation or composite waveforms. The first output waveform can be different than the second output waveform. The second output waveform can be periodically superimposed on the first output waveform. The controller can be in communication with the stimulation electrode. The controller can be configured to control application of the composite pattern of stimulation or waveform to a target site in a body of a subject suffering from a medical condition.

Another aspect of the present disclosure can include a method for neuromodulation to treat a medical condition in a subject. One step of the method includes applying composite patterns of stimulation or waveforms to a target site in the nervous system of the subject. The composite patterns of stimulation or waveforms include a first output waveform that is different than a second output waveform. The second output waveform is periodically superimposed on the first output waveform.

BRIEF DESCRIPTION OF THE DRAWINGS

The foregoing and other features of the present disclosure will become apparent to those skilled in the art to which the present disclosure relates upon reading the following description with reference to the accompanying drawings, in which:

In FIG. 1A, a rat is chronically housed inside a custom-made acrylic box cage (shown with the door open). The stimulation equipment is placed on the top of the acrylic box. The cables go through the roof of the box in a commutator, where the tethering system is connected. Inside the acrylic box there is a custom-made rat cage (approved by BRU/veterinarians). This rat cage is built with the slot for performance of the pasta matrix task so that the rat is not removed from its own environment at the time of performing the task. In addition, the cage is prepared to receive the pre-loaded pasta matrix apparatus (in black). In FIG. 1B, the tethered rat can easily reach the pasta matrix apparatus without constraints due to the tethering. Note that the pasta matrix task, just like the Montoya task, allows for evaluation of the left and right paws independently. In this picture, the rat is using the right paw to reach the left side of the pasta matrix. After stroke induction, the pasta is placed only on the side opposite to the affected hand to force testing with the affected hand (there is no pasta made available to the non-affected hand);

FIG. 3A is an illustration of lesion size in an animal with the mean stroke volume for this study (10 $mm^3$) (sections are presented every mm). FIG. 3B shows localization of implanted electrodes for animals that received stimulation;

In FIG. 3A, the total number of pasta pieces consumed over the three weeks is shown. By the second week, there was a non-significant trend for improved performance in the STIM group and by the third week this was significant ($p<0.01$). In FIG. 3B, the percent change in performance on this task over three weeks, which was significant at both weeks two and three ($p<0.05$, $p<0.001$);

FIG. 5 shows pasta matrix task performance. Each of the nine pictures represents half of the pasta matrix, filled with pasta on the side contralateral to the affected paw. Each cell represents one piece of pasta. The bottom left corner is the closest point to the slot in the cage where the rat's paw goes through, the upper right corner is the furthest point. The columns represent the performance at weeks one (left column), week three (middle), and the difference between weeks three and one (right column). The SHAM (no stim) group is shown in the upper row, the STIM group is shown in the middle, and the difference between the two in the lower row. In the no stimulation group, there are a few cells with non-significant improved performance in the proximal part of the matrix (seen in yellow in the difference between weeks three and one), but there are more cells in blue showing an overall decline in performance. In the STIM group, there is a gain in performance on most cells which is significant in two individual cells. In comparing the performance at the third week between STIM and SHAM groups (bottom row, middle column), there are several individual cells showing a significant difference between STIM and SHAM groups; and FIG. 6 is a graph showing performance in the pasta matrix over five weeks. Comparison of the task in animals receiving SHAM stimulation, 30 Hz isochronous stimulation, and 30 Hz with superimposed bursting. Note that the performance of animals in SHAM remains stable with no significant variance. However, animals in 30 Hz show more upward variance in performance. In the 30 Hz with superimposed bursting group, there are even greater improvements in performance. The magnitude of the effect is quite large but, due to the sample size, the effect is not significant when the three groups are compared with the current sample. However, the effects are significant when 30 Hz stimulation is compared to SHAM and when bursting stimulation is compared to 30 Hz stimulation.

DETAILED DESCRIPTION

The present disclosure relates generally to neuromodulation using electrical stimulation, and more particularly to neuromodulation using composite patterns of stimulation or composite waveforms to treat medical conditions. The present disclosure is based, at least in part, on the discovery that periodic bursting stimulation is more effective in motor recovery following a neurological insult than regular isochronous stimulation. Without being bound by theory, it is believed that periodic bursting stimulation may improve motor recovery by more closely resembling the natural activity of the cerebellar output than regular isochronous stimulation. Additionally or alternatively, periodic bursting stimulation may improve motor activity by causing long-term potentiation phenomena, which then facilitates the effects of regular isochronous stimulation. Based on this discovery, the present disclosure includes a method for deep brain stimulation of neural pathways and/or select brain regions to treat medical conditions. As described below, the present disclosure coordinates delivery of specific patterns of electrical stimulation, which are derived or obtained from a source subject based on the function or activity of other nervous system areas and/or body parts.

In one aspect, the present disclosure includes a method for neuromodulation to treat a medical condition in a subject using one or a combination of the same or different composite patterns of stimulation or waveforms. As described in more detail below, the composite patterns of stimulation or waveforms include at least two different waveforms, i.e., a first output waveform that has at least one parameter (e.g., frequency, duration, amplitude, phase symmetry, duty cycle) that is different from a corresponding parameter of a second output waveform. The first and second output waveforms are obtained from first and second input waveforms, respectively (described below). The first and second output waveforms can be identical to, or derived from, the first and second input waveforms (respectively). As described in more detail below, the second output waveform is periodically superimposed on the first output waveform to produce periodic bursting stimulation. It will be appreciated that the composite patterns of stimulation or waveforms can include two, three, four or even more output waveforms overlaid on the first output waveform.

Although not shown, it will be appreciated that the present disclosure can be implemented using one or a combination of neurostimulation systems (e.g., deep brain stimulation systems). In some instances, the present disclosure can be implemented using a stimulation system that is identically or similarly configured as disclosed in U.S. Pat. No. 8,112,154 to Machado et al., the entirety of which is hereby incorporated by reference. In one example, a neurostimulation system for treating a medical condition in a subject can comprise: a memory that stores waveform data for first and second input waveforms; a playback system that provides first and second output waveforms, based on the first and second input waveforms in the memory, to form a composite pattern of stimulation or waveform, the first output waveform being different than the second output waveform, the second output waveform being periodically superimposed on the first output waveform; a stimulation electrode; and a controller in communication with the stimulation electrode, the controller being configured to control application of the composite pattern of stimulation or waveform to a target site in a body of the subject suffering from the medical condition.

In some instances, the playback system can be configured to modify the first and/or second input waveforms to form the first and/or second output waveforms. For example, the first and/or second input waveform(s) may be modified by the playback system in various ways (discussed below) to produce the first and/or second output waveform(s) (respectively).

In other instances, the neurostimulation system can further comprise a sensor for sensing a bodily activity. In one example, the controller can control application of the composite pattern of stimulation or waveform in response to a sensed bodily activity.

As used herein, the term "waveform" can refer to the amplitude versus time relationship for an electrical signal, and may encompass one or more periods of a given signal. A waveform can be a recorded signal, which can be sampled and stored. Alternatively, a waveform can be generated by a waveform generating device (e.g., computer software or other waveform generator). For example, a waveform generator can construct or derive a waveform from a mathematical formula or based on a drawing or other visualization of a waveform that may be displayed on a screen. The term "waveform" can also include neuroelectrical coding for communication (e.g., the sequence, timing, pattern, or frequency of neural firings). Waveform data in a memory can be preprogrammed, such as prior to implantation, or programmed post-implantation of a stimulation system.

In another aspect, the present disclosure includes recording first and second input waveforms. The first and/or second input waveform(s) can be recorded from a first site in the nervous system of a source subject. In some instances, the second input waveform is obtained by recording an actual signal generated by a signal source site (or first site) in a human or animal body. The signal source site may be any part of the nervous system, including the central nervous system and peripheral nervous system (including the innervations at the end organs). These neural electrical signals may be known to control and/or regulate various body systems, including the nervous system, musculoskeletal system, endocrine system, immune system, pulmonary system, cardiovascular system, gastrointestinal system, or genitourinary system. As such, a recorded second input waveform may be associated with controlling and/or regulating a certain bodily activity or activities.

In some instances, the first and/or second input waveform recording is obtained from a site in the brain. Various parts of the brain may be the signal source site, such as the brain stem, cerebral cortex, subcortical cerebral structures, cerebellum including the deep cerebellar nuclei, basal ganglia, dentate, thalamus, or any component of the dentato-thalamo-cortical pathway or cortico-ponto-cerebellar pathway. In other cases, the first and/or second input waveform recording is obtained from the motor cortex, premotor cortex, thalamus, red nucleus, olivary nucleus, or dentate nucleus.

The first and/or second input waveform may be obtained from various human and non-human source subjects. In some instances, the source subject is the same as the subject suffering from the medical condition (i.e., the subject who is receiving neurostimulation). In such cases, the first and/or second input waveform may be obtained from a portion of the subject's nervous system that is healthy or at least partially functional. For example, where one part of the subject's brain is diseased (e.g., due to a stroke or trauma), the first and/or second input waveform may be obtained from the corresponding contralateral brain structure that is not affected by the disease. In other instances, the source subject and the subject suffering from the medical condition are not the same. For example, the subject suffering from the medical condition may be a person, while the source subject may be another person or an animal, such as a non-human primate.

The first and/or second input waveform may be obtained from the source subject in various settings. In some instances, the first and/or second input waveform is recorded from the source subject while undergoing surgery, such as brain surgery, spinal surgery, or peripheral nerve surgery. The source subject may be conscious, sedated, or under anesthesia during the surgery. In other instances, the first and/or second input waveform is recorded from the source subject while at rest or while performing an activity or task. Such tasks include forelimb (upper extremity) tasks and hindlimb (lower extremity) tasks. For example, forelimb tasks include reaching, grabbing, picking with opposable thumbs, grip squeezing, and hindlimb tasks, such as walking. In some cases, a plurality of recordings is made to form a library of waveform recordings, with each recording associated with a specific task, disease or condition.

In another aspect, the present disclosure includes obtaining first and second output waveforms from first and second input waveforms, respectively. The first and/or second output waveform(s) may be identical to, or derived from, the first and/or second input waveform(s) by modifying the first and/or second input waveform(s), respectively. One or both of the first and second input waveform may be modified in various ways to produce the first and second output waveform(s) (respectively). For example, the first and/or second input waveform may be modified to have a different pattern, intensity, amplitude, frequency, duration, pulse width, or number of pulse trains. In another example, additional pulses may be added to the first and/or second input waveform. The additional pulses may be added within the waveform or between waveforms. The additional pulses may be at pre-determined positions in the first and/or second input waveform, at pre-determined intervals, or triggered by a spike in the first and/or second input waveform. In another example, the first and/or second input waveform may be modified by copying, cutting, pasting, deleting, cropping, appending, or inserting desired segments of waveforms. In another example, the first and/or second output waveform can be obtained from different signal source sites, different source subjects, or different time points at the same signal source site.

In one example, the first output waveform can be characterized by a pattern of isochronous stimulation pulses (e.g., regular stimulation at about 30 Hz) and be obtained from a first input waveform that has been generated by an oscillator or other waveform generator. Alternatively, a period comprising the first input waveform can be characterized by evenly-spaced apart stimulation pulses. For regular 30 Hz stimulation, for example, each of the 30 pulses can be evenly distributed during the duration of one second. In another instance, a period comprising the first input waveform can be characterized by randomly spaced-apart stimulation pulses (e.g., during the duration of one second), which may represent nature more closely. Another option can include placing substantially all of the pulses at the beginning or the end of the period comprising the first input waveform. It will be appreciated that the frequency of the first input waveform can vary from about 0.1 Hz to about 1000 Hz.

In another example, the second output waveform is characterized by at least one parameter (e.g., frequency, duration, amplitude, phase symmetry, duty cycle) that is greater or less than the corresponding parameter of the first output waveform. For example, the second output waveform can have a frequency and/or duration that is/are greater or less than the frequency and/or duration of the first output waveform to yield periodic bursting stimulation. It will be appreciated that the second output waveform can have a frequency of about 1 Hz to about 1000 Hz, and a duration of about 1 ms to about 1000 seconds. As noted above, the second output waveform is periodically superimposed on the first output waveform. For example, the second output waveform can be periodically superimposed on the first output waveform at a regular interval or, alternatively, at an irregular interval. As also noted above, the composite patterns of stimulation or waveforms can include two, three, four or even more output waveforms overlaid on the first output waveform. For example, a first output waveform of about 30 Hz can be overlaid with multiple output waveforms characterized by intermittent bursts of about 70 Hz, 100 Hz and 250 Hz.

In another aspect, composite patterns of stimulation or waveforms can be applied as neurostimulation to one or more target sites in the body of a subject suffering from a medical condition. A target site can include any part of the nervous system, including the central nervous system and the peripheral nervous system. In some instances, the target site is a cerebellar pathway (e.g., extending between the cerebellum and the cerebral cortex via the thalamus, brain stem, or other subcortical structure(s)). In other cases, the target site is a structure in the brain, such as the brain stem, cerebral cortex, subcortical cerebral structures, cerebellum including the deep cerebellar nuclei, basal ganglia, dentate, thalamus, or any component of the dentate-thalamo-cortical pathway. In other cases, the target site is the motor cortex, premotor cortex, thalamus, red nucleus, olivary nucleus, or dentate nucleus.

In some instances, the nervous system structure representing the target site anatomically corresponds to the nervous system structure representing the signal source site. For example, a second input waveform can be obtained for one thalamus in one subject, and the second output waveform can be applied (as part of the composite waveform) to another thalamus in another subject. In other instances, the nervous system structure representing the target site is anatomically different from the nervous system structure representing the signal source site. The target site may be neurologically proximal or distal to the signal source site; or, where the source subject and the subject suffering from the medical condition are different, the target site may anatomically correspond to a structure that is neurologically distal to the signal source site. For example, a second input waveform recording can be made in a thalamus, and the second output waveform can be applied (as part of the composite patterns of stimulation or waveforms) to a cerebral cortex.

Composite patterns of stimulation or waveforms may be applied as neurostimulation using any of various conventional means. In some cases, the stimulation is applied by direct conduction. For example, the stimulation can be performed with an electrode positioned at the target site. The electrode can be implanted permanently, chronically or temporarily. In other cases, the stimulation is applied externally or without direct contact with the target site structure. For example, the neurostimulation may be performed using a probe that transmits electromagnetic energy (e.g., RF) that is captured by the target site.

In another aspect, delivery of composite patterns of stimulation or waveforms to a target structure is coordinated with the activity of a brain area or body part. Currently, deep brain stimulation applications deliver constant isochronous stimulation to a brain target regardless of what the patient is doing (e.g., resting, sleeping, moving an arm, walking, etc.). Unlike conventional methods, the stimulation pattern(s) delivered by the present disclosure is/are delivered to a target structure at each moment depending on the activity of a given brain area (which could be the same as or different than the target structure) or another body part. To accomplish coordinated delivery of electrical stimulation, at least one of a bodily activity or a nerve activity associated with a bodily activity of the subject suffering from the medical condition is sensed. The bodily activity and/or nerve activity can be sensed by a sensor. The bodily activity or associated nerve activity can include any characteristic or function of the subject's body (including bodily organs), such as mechanical motion, electrical, or chemical activity. For example, the sensor may sense that a body part is moving or beginning to move (e.g., via electromyography or a nerve electrode), such as at the onset of walking or speech. The sensed activity can then trigger stimulation at a target site. Alternatively, the activity of another area of the brain, such as the premotor cortex can cause the pattern(s) of stimulation at a target site to change.

Other examples of bodily activities and physiological parameters that are indicative of particular bodily activities, and that may be sensed by the claimed disclosure, can include, but are not limited to: gastrointestinal function, such as gastric acid concentration, intestinal motility, and peristalsis; temperature; respiratory function; heart rate; capillary pressure; venous pressure; perfusion; blood gases, such as carbon dioxide including partial pressure of carbon dioxide; oxygenation including blood oxygenation levels, oxygen saturation levels partial pressure of oxygen, oxygen consumption, oxygen pressure; water pressure; nitrogen pressure; carbon dioxide pressure in the tissue; circulation (including blood and lymphatic); electrolyte levels in the circulation/tissue; diffusion or metabolism of various agents and molecules (such as glucose); neurotransmitter levels; body temperature regulation; blood pressure; blood viscosity; metabolic activity; cerebral blood flow; pH levels; vital signs; galvanic skin responses; perspiration; electrocardiogram; electroencephalogram; action potential conduction; chemical production; body movement including limb movement, posture and gait; response to external stimulation; cognitive activity; dizziness; pain; flushing; motor activity including muscle tone; visual activity; speech; balance; diaphragmatic movement; chest wall expansion; and concentration of certain biological molecules/substances in the body, such as glucose, liver enzymes, electrolytes, hormones, creatinine, medications, concentration of various cells, platelets or bacteria. These bodily activities can be measured utilizing a variety of methods including, but not limited to, chemical analysis, mechanical measurements, motion sensors, laser, and fiber-optic analysis.

In response to the sensed bodily activity or nerve activity associated with a bodily activity, the second output waveform can be triggered or modified. The second output waveform can be triggered or modified by a sensor that senses that a body part is moving or beginning to move. For example, the second output waveform can be triggered or modified by the onset of walking or speech. In other instances, the second output waveform can be triggered or modified by the activity of a brain area that is different than the target site. For example, if a particular activity is sensed in the premotor cortex (which is responsible for planning movement), the pattern of stimulation at the target site can change by triggering or modifying the second output waveform. It will be appreciated that stimulation may be reduced or stopped depending upon the sensed activity or activities.

In some instances, neurostimulation is applied while the subject suffering from the medical condition is performing a task. In this case, composite patterns of stimulation or waveforms can be selected based on the task being performed by the subject. Without intending to be bound by theory, it is believed that applying neurostimulation in this manner will facilitate rehabilitation by enhancing the natural process of neural plasticity.

The claimed disclosure can be used to treat a variety of conditions or disorders. Non-limiting examples of medical conditions that can be treated according to the present disclosure include genetic, skeletal, immunological, vascular or hematological, muscular or connective tissue, neurological, ocular, auditory or vestibular, dermatological, endocrinological, olfactory, cardiovascular, genitourinary, psychological, gastrointestinal, respiratory/pulmonary, neoplastic, inflammatory medical conditions, or any combination thereof. Further, the medical condition can be the result of any etiology including vascular, ischemic, thrombotic, embolic, infectious (including bacterial, viral, parasitic, fungal, abscessal), neoplastic, drug-induced, metabolic, immunological, collagenic, traumatic, surgical, idiopathic, endocrinological, allergic, degenerative, congenital, abnormal malformational causes, or combinations thereof.

With respect to treating neurological medical conditions, such medical conditions can involve any medical conditions related to the components of the nervous system, such as: the brain including the hemispheres, cerebellum, brain stem, pons, midbrain, medulla; the spinal cord; peripheral nerves; peripheral ganglia; and nerve plexuses. In one example, the medical condition can result from a neurological insult, such as a stroke or trauma (e.g., traumatic brain injury). Non-limiting examples of neurological conditions include neurodegenerative disorders, Alzheimer's disease, epilepsy, multiple sclerosis, ALS, Guillan Barre, neurovascular disorders including stroke, cerebral palsy, intracerebral hemorrhage, dementia, vertigo, tinnitus, diplopia, cerebral vasospasm, aneurysm, atriovenous malformation, brain malformations, movement disorders, multi-system atrophy, olivopontocerebellar degeneration, familial tremor dystonia including cervical dystonia, torticollis, facial dystonia, blepharospasms, spasmodic dysphonia, radiculopathy, neuropathic pain, sleep disorders, disorders of temperature regulation in the body and extremities, postherpetic neuralgia involving the face, head, body or extremities. The neuropathic pain may be caused by fracture, crush injury, compressive injury, repetitive movement injury, diabetes, trauma, alcohol, infection, or hereditary. The sleep disorder may be sleep apnea, restless leg syndrome, narcolepsy, snoring, insomnia, drowsiness, or suitable combinations thereof.

Non-limiting examples of movement disorder include or manifest as: ataxia, akinesia, athetosis, ballismus, hemiballismus, bradykinesia, dystonia, chorea including Huntington's disease, multiple system atrophies (e.g., Shy-Drager syndrome), myoclonus, Parkinson's disease, progressive supranuclear palsy, restless leg syndrome and periodic limb movement disorder, tics, Tourette's syndrome, tremor (e.g., essential tremor, resting tremor), Wilson disease, tardive dyskinesia, and paralysis or weakness due to stroke or other cortical injury.

Another aspect of the present disclosure can include a method for generating a composite pattern of stimulation or waveform. In some instances, a method for generating a composite pattern of stimulation or waveform can comprise: recording a first input waveform; recording a second input waveform from a first site in a nervous system of a source subject; and obtaining first and second output waveforms, respectively, from the first and second input waveforms. In some instances, the first and second output waveforms are identical to, or derived from, the first and second input waveforms, respectively. In other instances, the method for generating a composite pattern of stimulation or waveform can be executed using the neurostimulation described herein. For example, the steps of recording first and second waveforms can be performed using a memory that stores waveform data, and the step of obtaining the first and second output waveforms can be performed using a playback system. Characteristics of the first and second output waveforms are described above.

The following examples are for the purpose of illustration only and are not intended to limit the scope of the claims, which are appended hereto.

EXAMPLE 1

Introduction

The goal of this study is to evaluate the effects of electrical stimulation of the dentatothalamocortical (DTC) pathway on motor recovery after focal ischemia. We have previously demonstrated that stimulation of the DTC pathway enhances motor recovery even after large ischemic strokes, resulting from microsurgical ligation of the middle cerebral artery in combination with temporary occlusion of the carotid arteries (3VO model) (Machado AG et al., Brain Res. 1280:107-16, July 2009). In addition, we have demonstrated that stimulation of the DTC pathway at the dentate nucleus increases contralateral cerebral cortex excitability (Baker KB et al., Exp Neurol. 226(2):259-64, December 2010). This effect was frequency-dependent, such that stimulation in the upper beta band proved to be the most effective for increasing cortical excitability.

Figure 1A:
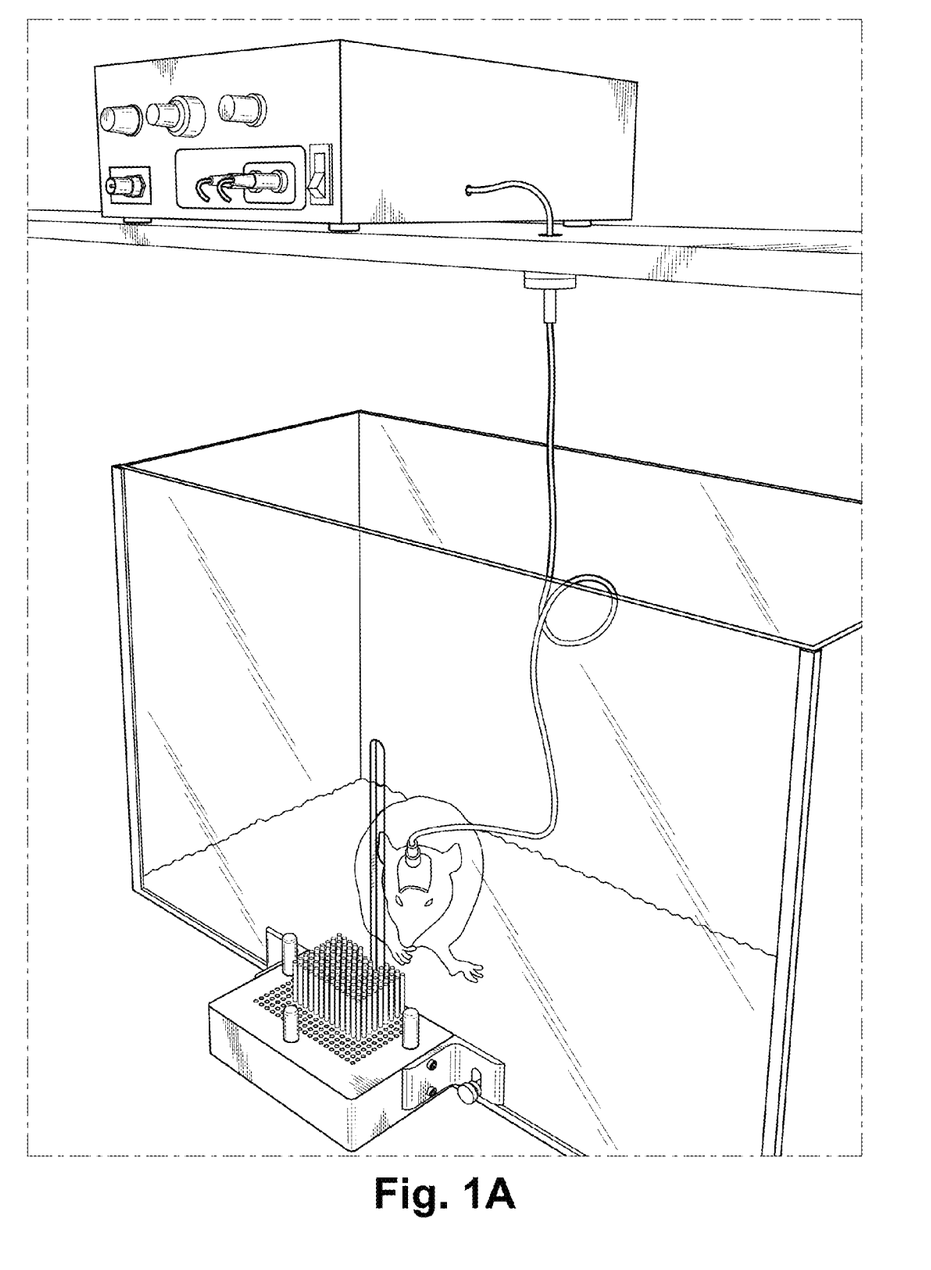
FIGS. 1A-B are photographs showing the animal set-up for a pasta matrix task.
Figure 1B:
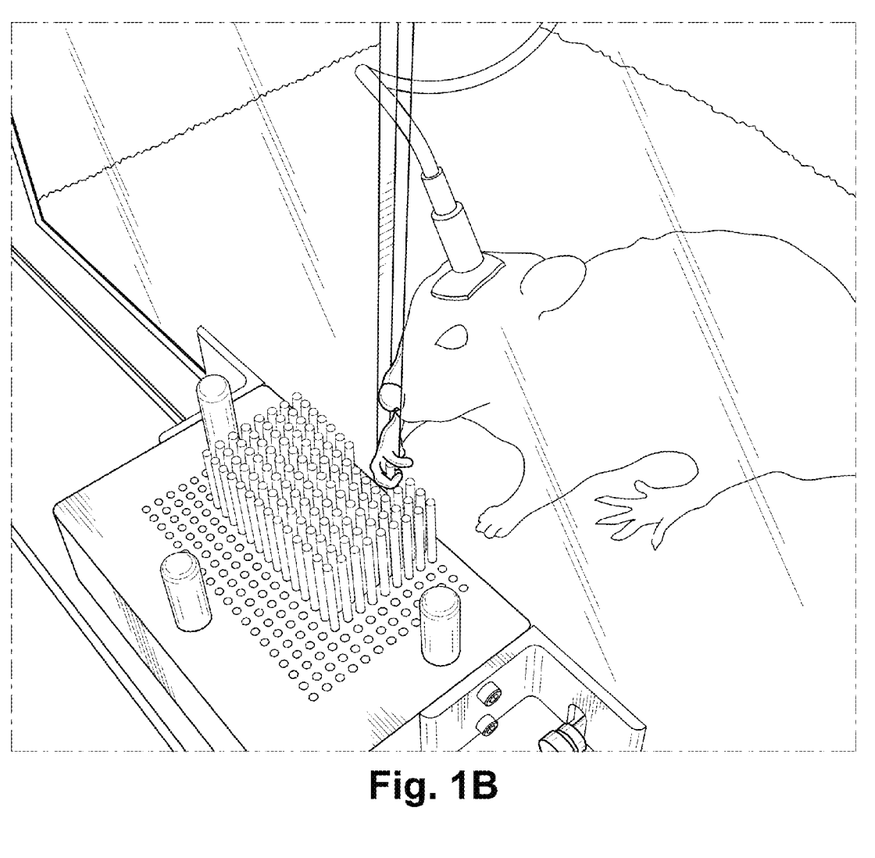

In our previous progress report for the first year, we reported the methodological changes that were completed in our laboratory to improve our neurorehabilitation stimulation paradigm. One methodological change that we implemented was a means of providing stimulation to the animals while they were performing their behavioral tasks. We have switched to the pasta matrix task, which proved to be successful for accomplishing our aim. FIGS. 1A-B represent our current set-up for stimulating the dentatothalamocortical system while training and testing on the motor task.

Studies and Results

Figure 2:
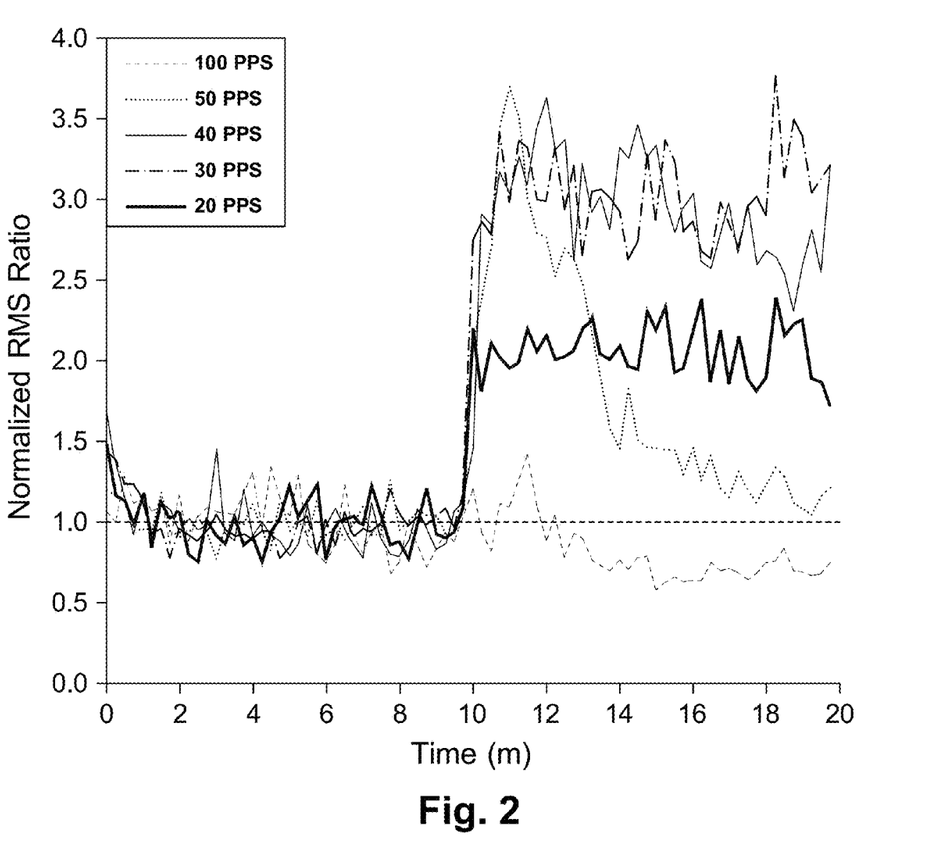
FIG. 2 is a graph showing frequency-dependent effects of lateral cerebellar nucleus stimulation on contralateral motor cortex excitability over time. Cortical excitability was indexed by the amplitude of MEP generated by intracortical microstimulation.

We had previously shown that stimulation of the dentatothalamocortical pathway enhances contralateral cerebral cortical excitability in a frequency dependent fashion. Stimulation at 30 Hz was shown to produce the most significant and sustained enhancement of excitability (FIG. 2). However, our previous behavioral results had been tested with stimulation at 10, 20 and 50 Hz, showing small but significant improvements in motor outcomes with stimulation at 20 Hz but not at 10 or 50 Hz. Further, this was tested with stimulation not paired to motor task training. In this year, our goals were to advance the previous research proposed by a) pairing stimulation at 30 Hz with training in the motor task and b) testing non-isochronous (i.e., regular or irregular bursting over a baseline frequency) stimulation.

30 Hz chronic stimulation of the dentatothalamocortical pathway paired with training in the pasta matrix task Forty-eight Sprague-Dawley rats (in two consecutive batches of 24) weighing 200-225 g were acclimatized to a custom made caging system and deprived to approximately 12 g/day of food.

All animals were then trained for three weeks in the pasta matrix task (Teskey G C et al., Neurol Res. 25(8):794-800, December 2003) for 20 min/day, 5 days week during the dark cycle under controlled infrared lighting. The dominant paw was based on the pattern of performance in the task. The animals are housed in the same cages where they undergo the pasta matrix task. When the task is completed the slot is covered with a custom plate.

After training was complete, animals were fast overnight and underwent endothelin-1 (ET-1) injections in the motor cortex contralateral to the dominant paw and contralateral implant of the deep cerebellar electrode under the same anesthetic procedure. Three bur holes were created over the dominant hemisphere at the planned injection sites. The coordinates for each of the 800 pmol ET-1 injections in relation to bregma were: 1) AP=−1.0 mm, ML=2.5 mm, DV=−2.3 mm, 2) AP=+1.0 mm, ML=2.5 mm, DV=−2.3 mm and 3) AP=+3.0 mm, ML=2.5 mm, DV=−2.3 mm. Each 800 pmol. ET-1 injection was diluted to 2 µl. The needle was inserted and the injection initiated after 1 min at a rate of 0.5 µl/min with a 1 min pause after 1 µl and a 3 min pause before withdrawing the needle (Windle V et al., Exp Neurol. 201(2):324-34, October 2006).

The electrode was implanted contralateral to the ET-1 injections with the same technique as previously described by our group (Machado AG et al., Brain Res. 1280:107-16, July 2009). Briefly, under the same anesthesia, a bur hole was created at the site of pre-determined coordinates (AP=−11.0 mm and ML=3.6 mm). The dura was punctured and the electrode descended to DV=−6.3 mm. Small stainless screws were placed in the calvaria away from the bur holes for injection or implantation. The screws and the electrode (Model MS306, Plastics One Inc., Roanoke, Va., USA) were incorporated with dental cement to the skull with the distal electrode connector exposed for connection to the commutator system. The animals were allowed to recover with food and water ad libitum for one week. Buprenorphine was used for analgesia.

All animals were then connected to the commutator system inside the same custom cages and assessed in the pasta matrix task (20 min/day) for five days. In the last day, the motor threshold for deep cerebellar stimulation was determined as previously reported (Baker KB et al., *Exp Neurol.* 226(2): 259-64, December 2010). Rats were then matched according to stroke severity indexed by post-stroke pasta matrix task performance and assigned to one of two groups: STIM (continuous isochronic 30 Hz stimulation at 80% of motor threshold for cerebellar stimulation); and SHAM (stimulation at 0V). Stimulation was always 12 h ON during the dark period and 12 h OFF. Rats were then evaluated over three additional weeks, undergoing pasta matrix task 10 min/day, 5 days/week during the dark period. All animals underwent the cylinder task once on each postoperative week. The task was recorded from the bottom for 10 min/session. Behavior was digitally video-recorded with a camera adapted to the bottom of each cage. Both the cylinder and pasta matrix tasks were given in the rat's own cage without disconnection to the tethering system or interruption of stimulation.

At the end of the experiments all animals underwent deep anesthesia with 50 mg/kg of pentobarbital and transcardiac perfusion with saline followed by 4% paraformaldehyde. Brain were then carefully removed and immersed in 4% paraformaldehyde. Brains were blocked in paraffin and sectioned at 40 μm. Every eighth cerebrum slice was mounted (320 μm gaps) and Nissl stained for stroke size calculation and every cerebellar slice was mounted and Perls iron stained for verification of electrode localization. Prior to sacrifice a minor lesion was created at the site of implant with electrocoagulation (1.0 mA, DC current, 15 s).

Results

Forty-two animals underwent ischemia and electrode implantation. Twenty-four animals completed post-stroke evaluation with the pasta matrix and cylinder tasks. Eighteen animals were lost due to either poor performance on the behavioral task, death, infection or dislodgement of the cerebellar electrode.

Histology

Figure 3A:
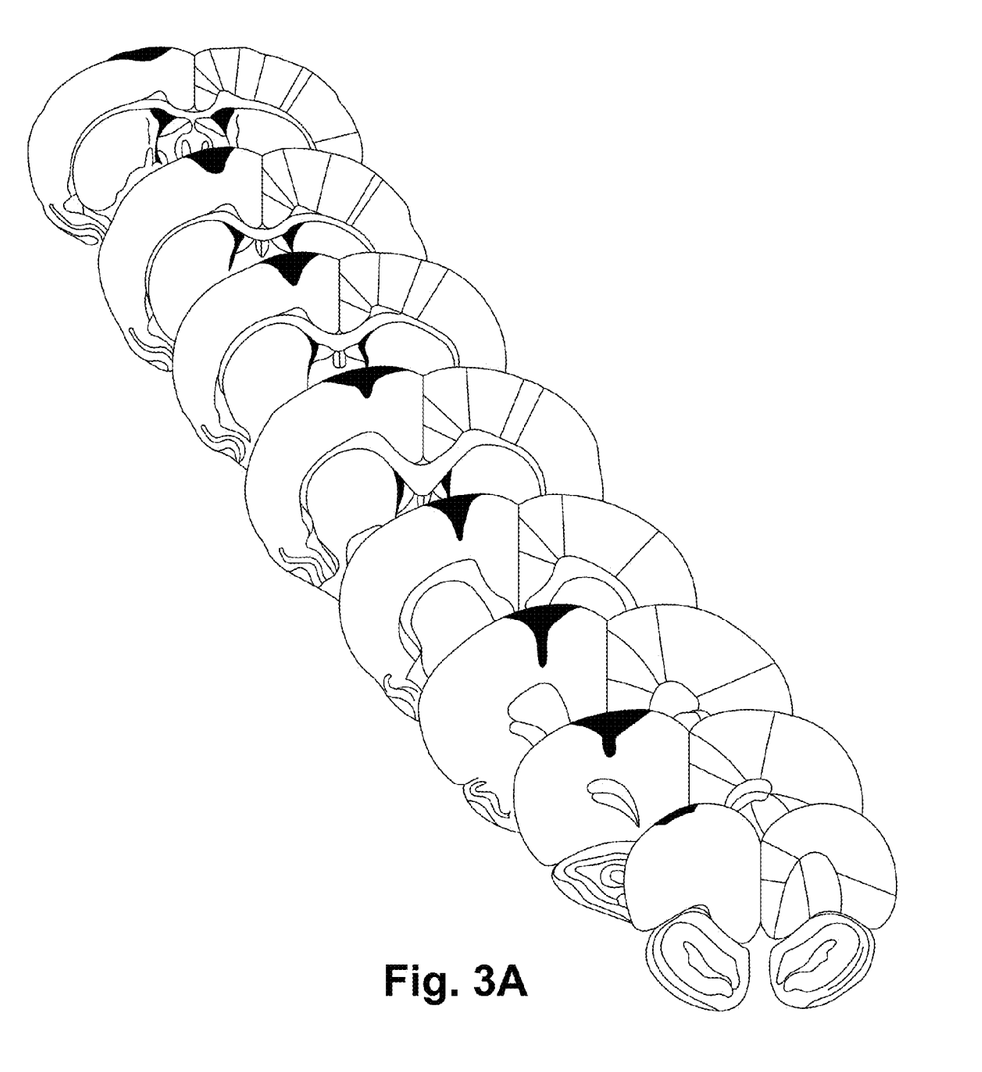
FIGS. 3A-B illustrates a typical stroke and a sampling of electrode locations.
Figure 3B:
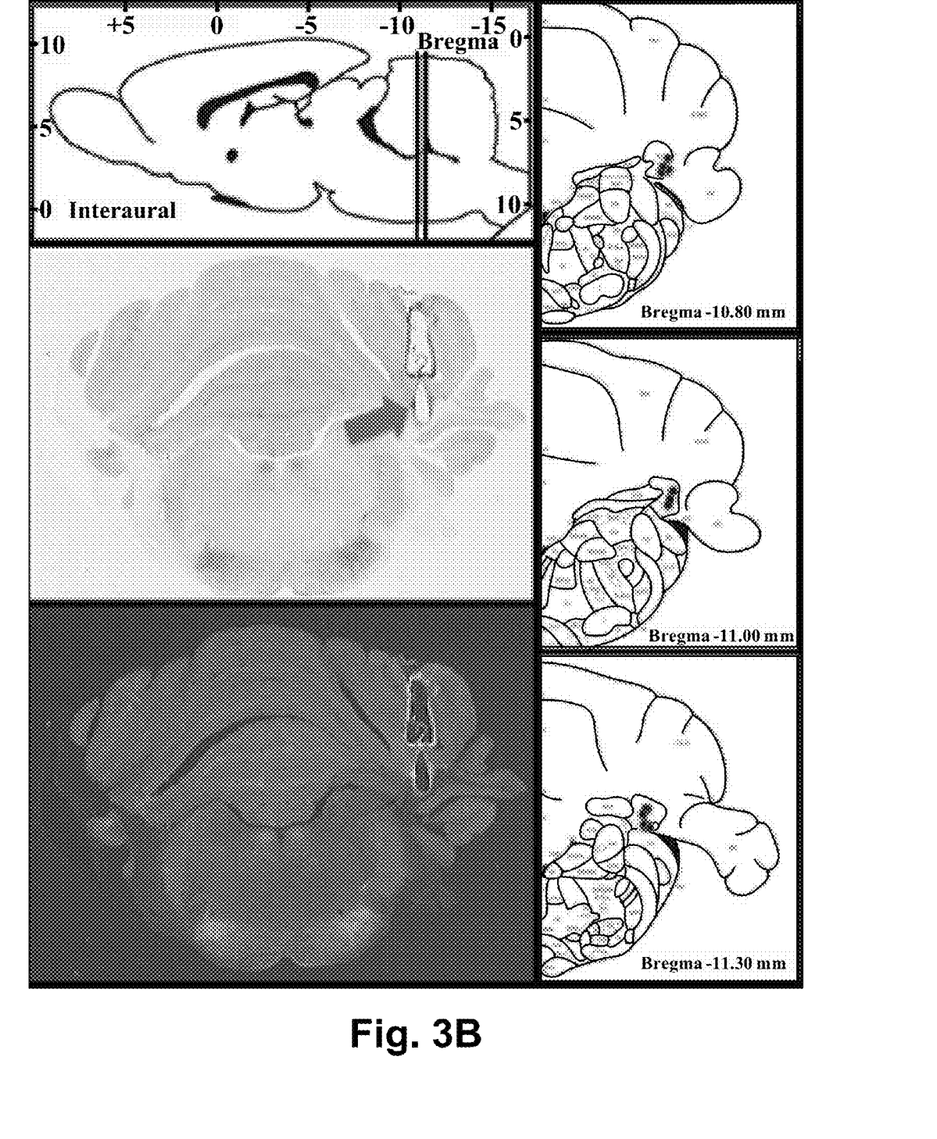

All animals that completed evaluation had strokes measured and electrode location verified by histological examination. The overall average stroke volume was $8.9 \pm 1.9$ mm$^3$ (mean±SEM); the overall average stroke volume in the STIM group was $7.2 \pm 1.8$ mm$^3$ and in the SHAM group was $10.1 \pm 3.1$ mm$^3$. Electrode implantation was evaluated by comparing the location of the artifact from the tip of the electrode and minor electrolytic lesion to the topography of the LCN in the Paxinos and Watson atlas (Paxinos and Watson, *The Rat Brain in Stereotaxic Coordinates*, 4$^{th}$ Ed. Academic Press 1998) of the rat brain. All electrodes were within the target area. FIG. 3 illustrates a typical stroke and a sampling of electrode locations.

Pasta Matrix

Figure 4A:
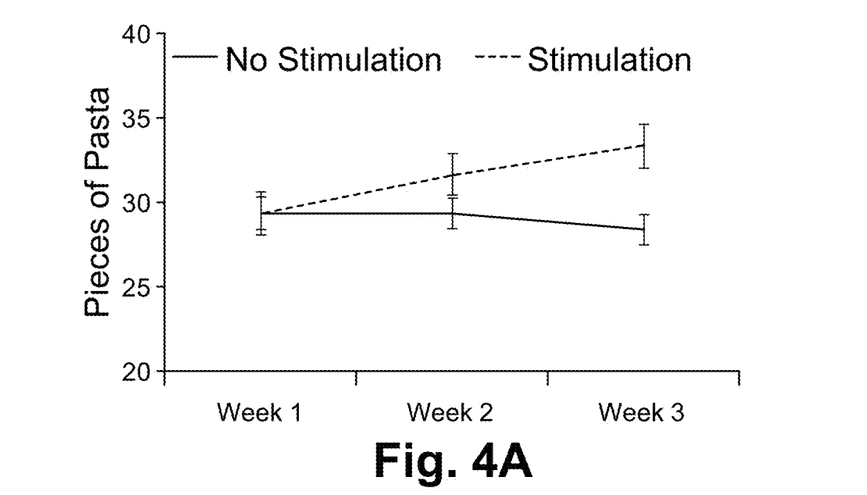
FIGS. 4A-B are a series of graphs showing performance in the pasta matrix over three weeks.
Figure 4B:
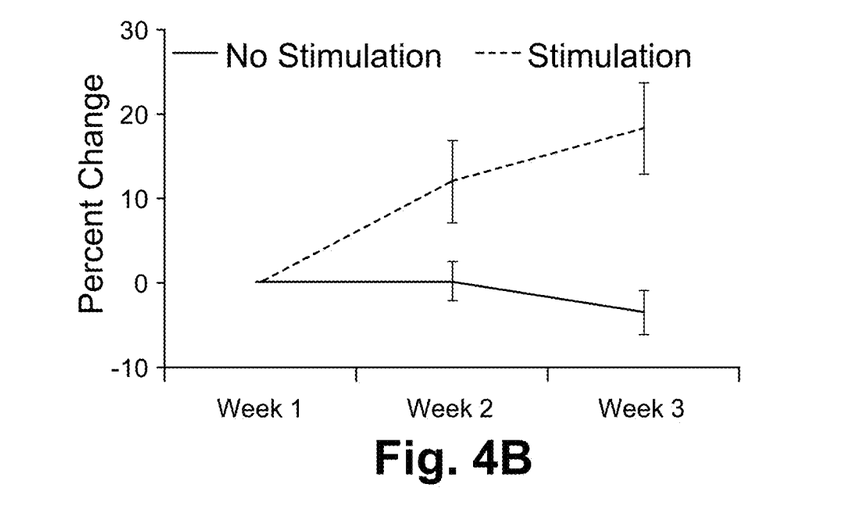

There was no significant difference between the two groups prior to stimulation onset or during the first week of stimulation ($29.3 \pm 1.0$ and $29.3 \pm 1.3$ pieces of pasta; STIM and SHAM groups respectively). At the end of the second week of stimulation, animals in the STIM group ate $31.6 \pm 1.2$ pieces of pasta ($p<0.05$ relative to week 1) with the affected hand while those in SHAM ate $29.9 \pm 0.9$ (no significantly different than week). At the end of the third week, animals in the STIM group ate $33.3 \pm 1.3$ pieces of pasta with the dominant (affected) hand while those in SHAM only ate $28.4 \pm 0.9$ pieces. In addition, comparing the first and third weeks of post-stroke stimulation in the SHAM group, we note a non-significant decline in performance ($p=0.08$). In contrast, the STIM group showed significant improvement in performance comparing the third and first weeks ($P<0.001$). The results are illustrated in FIG. 4.

Figure 5:
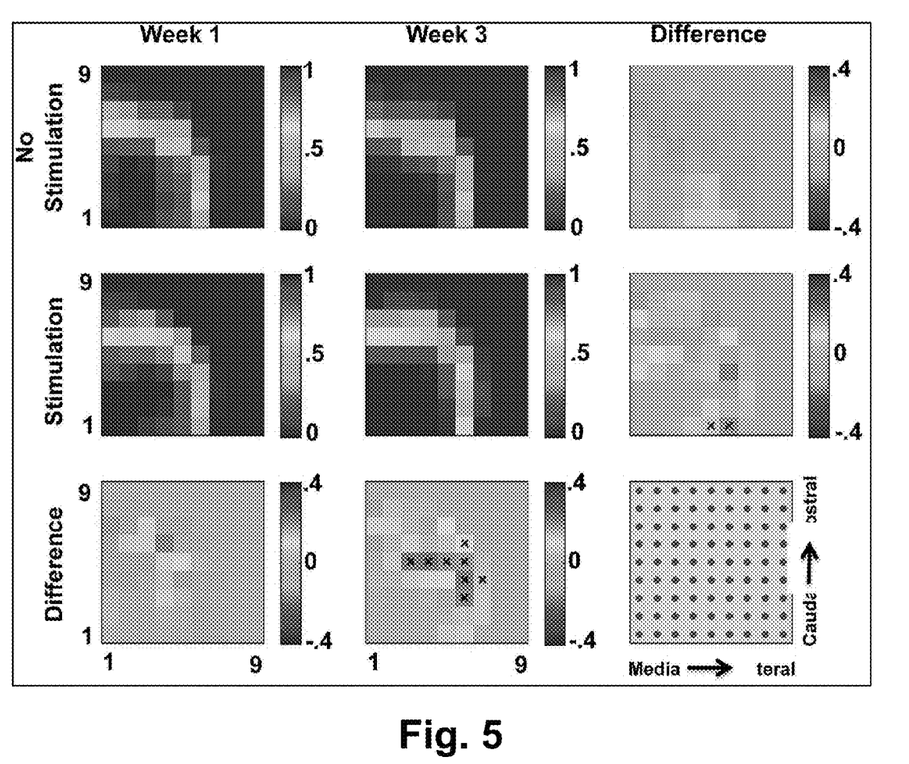

We further evaluated the pattern of change in performance in the two dimensions of the task to evaluate if animals were globally improving or if there was a preferential direction of functional gains. Regardless of the preferential side, all matrices were plotted on overlaying templates as illustrated in FIG. 5. Rats in the SHAM group presented with loss of function predominantly in the antero-medial quadrant of the matrix. This also occurred on two isolated cells in the STIM group. However, in the latter there were greater gains to pasta consumption anteriorly and laterally, resulting in a total net gain. There were several individual cells with significantly greater pasta consumption in the STIM groups (FIG. 5).

EXAMPLE 2

Figure 6:
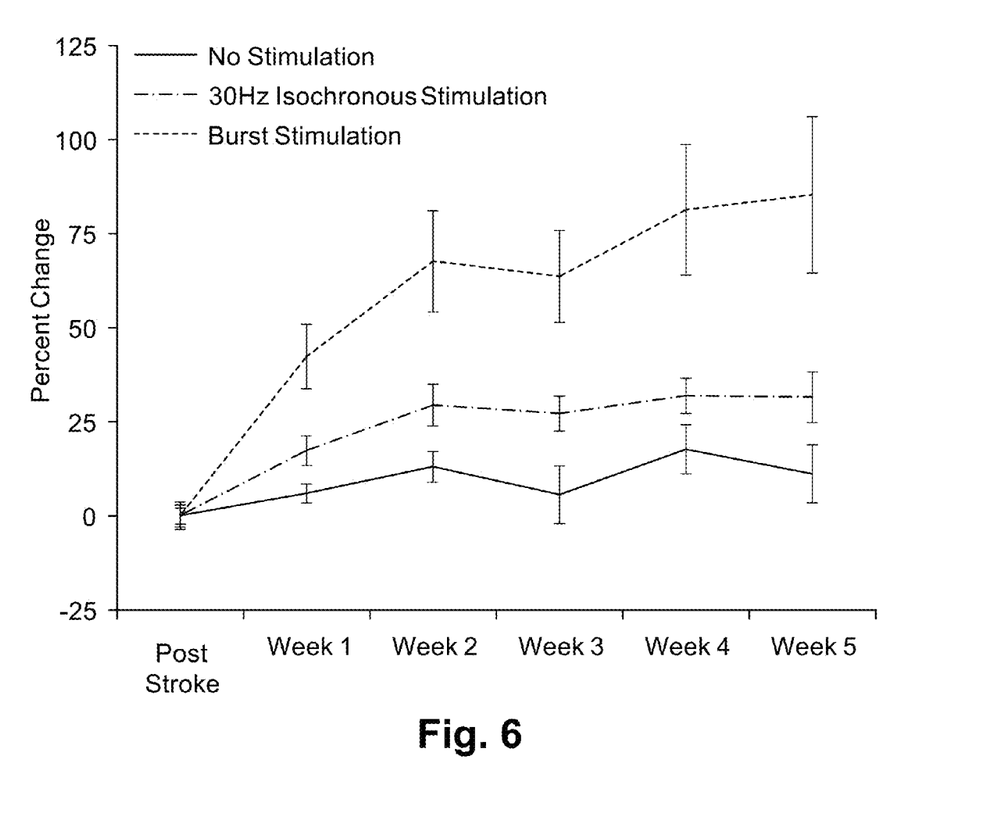

The same methods for implantation, stroke and stimulation as described in Example 1 were repeated, except that stimulation was carried to 5 weeks post-stroke. There were 8 animals assigned to the non-isochronous stimulation paradigm, with 100 Hz bursts superimposed on 30 Hz continuous stimulation, 8 animals receiving the regular 30 Hz stimulation sequence and 5 rats receiving SHAM (no stimulation). Over the five weeks, there were non-significant improvements in task performance in the 30 Hz stimulation group compared to SHAM. In addition, there were non-significant improvements in task performance of animals receiving bursting stimulation compared to regular 30 Hz stimulation and to SHAM. FIG. 6 summarizes these results.

From the above description of the present disclosure, those skilled in the art will perceive improvements, changes and modifications. Such improvements, changes, and modifications are within the skill of one in the art, and are intended to be covered by the appended claims.

The following is claimed:

1. A neurostimulation system comprising: memory that stores data for first and second input waveforms; a playback system that provides first and second output waveforms, based on the first and second input waveforms in the memory, respectively, to form composite patterns of stimulation or waveforms, the first output waveform comprising randomly spaced-apart pulses, the second output waveform periodically superimposed on the first output waveform at irregular intervals, the second output waveform having a greater frequency than the first output waveform.

2. The system of claim 1, further comprising a sensor for sensing a bodily activity.

3. The system of claim 1, wherein the waveform data stored in the memory is associated with the performance of specific physical tasks.

4. The system of claim 1, wherein the first and second output waveforms are identical to or derived from the first and second input waveforms.

5. A method for neuromodulation to treat a medical condition in a subject comprising: applying composite patterns of stimulation or waveforms to a target site of a cortico-ponto-cerebellar pathway or a dentate-thalamo-cortical pathway in the nervous system of the subject, the composite patterns of stimulation or waveforms comprising a first output waveform and a second output waveform, the first output waveform comprising randomly spaced-apart pulses, the second output waveform periodically superimposed on the first output waveform at irregular intervals, the second output waveform having a greater frequency than the first output waveform, wherein delivery of the second output waveform is triggered by a sensed bodily activity.

6. The method of claim 5 further comprising:
recording a first input waveform;
recording a second input waveform from a first site in the nervous system of a source subject; and
obtaining the first and second output waveforms, respectively, from the first and second input waveforms.

7. The method of claim 6, wherein the first and second output waveforms are identical to or derived from the first and second input waveforms, respectively.

8. The method of claim 6, wherein the source subject and the subject suffering from the medical condition are different subjects.

9. The method of claim 6, wherein the source subject and the subject suffering from the medical condition are the same subject.

10. The method of claim 6, wherein the first site anatomically corresponds to the target site.

11. The method of claim 6, wherein the first site is anatomically different than the target site.

12. The method of claim 6, wherein the first site is healthy or at least partially functioning, and the target site is diseased.

13. The method of claim 6, further comprising modifying the second input waveform to generate the second output waveform.

14. The method of claim 5, wherein the medical condition results from a neurological insult.

15. The method of claim 14, wherein the neurological insult includes trauma or stroke.

16. The method of claim 5, wherein the target site comprises a cerebellar pathway or pathway from the cerebral cortex to the cerebellum or cerebellum to the cerebral cortex.

17. The method of claim 5, wherein a substantial number of stimulation pulses comprising a period of the first output waveform occur at the beginning of the period.

18. The method of claim 5, wherein a substantial number of stimulation pulses comprising a period of the first output waveform occur at the end of the period.

19. The method of claim 5, wherein the second output waveform is characterized by a duration that is greater or less than the duration of the first output waveform.

20. The method of claim 5, further comprising, in response to the sensed bodily activity or nerve activity associated with a bodily activity, modifying the second output waveform.

21. The method of claim 5, wherein the composite pattern of stimulation or waveforms comprising a first output waveform that is overlaid with multiple output waveforms.

22. The method of claim 5, wherein the target site is a site of the cortico-ponto-cerebellar pathway or the dentate-thalamo-cortical pathway and the sensed bodily activity is sensed from a site different than the target site of the cortico-ponto-cerebellar pathway or the dentate-thalamo-cortical pathway.

23. The method of claim 5, wherein the target site is a site of the cortico-ponto-cerebellar pathway or the dentate-thalamo-cortical pathway and the sensed bodily activity is sensed from a site that is the same as the target site of the cortico-ponto-cerebellar pathway or the dentate-thalamo-cortical pathway.

24. A neurostimulation system comprising:
memory that stores data for first and second input waveforms; a playback system that provides first and second output waveforms, based on the first and second input waveforms in the memory, respectively, to form composite patterns of stimulation or waveforms, the first output waveform comprising randomly spaced-apart pulses, the second output waveform periodically superimposed on the first output waveform at irregular intervals, the second output waveform having a greater frequency than the first output waveform;
a stimulation electrode; and
a controller in communication with the stimulation electrode, the controller being configured to control application of the composite patterns of stimulation or waveforms to a target site in a body of a subject suffering from a medical condition.

* * * * *